(12) United States Patent
Casscells et al.

(10) Patent No.: US 6,993,382 B2
(45) Date of Patent: *Jan. 31, 2006

(54) METHOD OF DETECTING VULNERABLE ATHEROSCLEROTIC PLAQUE

(75) Inventors: S. Ward Casscells, Houston, TX (US); James T. Willerson, Houston, TX (US); Gregory H. Bearman, Pasadena, CA (US); Michael L. Eastwood, So. Pasadena, CA (US); Timothy N. Krabach, Valencia, CA (US)

(73) Assignee: Board of Regents The University of Texas System, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 10/222,342

(22) Filed: Aug. 16, 2002

(65) Prior Publication Data

US 2003/0004430 A1 Jan. 2, 2003

Related U.S. Application Data

(60) Continuation of application No. 09/268,609, filed on Mar. 15, 1999, now Pat. No. 6,475,159, which is a division of application No. 08/717,449, filed on Sep. 20, 1996, now Pat. No. 5,935,075.

(60) Provisional application No. 60/004,061, filed on Sep. 20, 1995.

(51) Int. Cl.
*A61B 5/04* (2006.01)

(52) U.S. Cl. .................................. 600/545
(58) Field of Classification Search ............ 600/549, 600/474, 477, 478; 606/15, 7
See application file for complete search history.

(56) References Cited

U.S. PATENT DOCUMENTS

| | | | |
|---|---|---|---|
| 3,273,395 A | 9/1966 | Schwarz |
| 3,638,640 A | 2/1972 | Shaw |
| 3,866,599 A | 2/1975 | Johnson |
| 3,913,568 A | 10/1975 | Carpenter |
| 4,005,605 A | 2/1977 | Michael |
| 4,200,110 A | 4/1980 | Peterson et al. |
| 4,281,645 A | 8/1981 | Jobsis |
| RE32,204 E | 7/1986 | Halvorsen |
| 4,602,642 A | 7/1986 | O'Hara et al. |
| 4,699,147 A | 10/1987 | Chilson et al. |
| 4,752,141 A | 6/1988 | Sun et al. |

(Continued)

FOREIGN PATENT DOCUMENTS

EP 0392897 4/1990

(Continued)

OTHER PUBLICATIONS

Wike-Holley, J.L. et al. The Relevance of Tumour pH to the Treatment of Malignant Disease, Radiotherapy and Oncology, 2 (1984) 343-366.

(Continued)

*Primary Examiner*—Max F. Hindenburg
*Assistant Examiner*—Brian Szmal
(74) *Attorney, Agent, or Firm*—Bruce M. Canter

(57) ABSTRACT

A method of detecting vulnerable arterial plaque formed on the vessel wall in vivo is disclosed. The method comprises obtaining an image of the arterial plaque, measuring the temperature of the arterial plaque, and determining whether the plaque exhibits an elevated temperature compared to the temperature of at least one adjacent vessel wall site. The method may include determining whether the plaque exhibits an elevated temperature of between 0.4 to 4° C. above at least one adjacent vessel wall site.

7 Claims, 6 Drawing Sheets

U.S. PATENT DOCUMENTS

| | | | |
|---|---|---|---|
| 4,776,334 A | 10/1988 | Prionas | |
| 4,777,955 A | 10/1988 | Brayton et al. | |
| 4,784,149 A | 11/1988 | Berman et al. | |
| 4,790,324 A | 12/1988 | O'Hara et al. | |
| 4,794,931 A | 1/1989 | Yock | |
| 4,797,840 A | 1/1989 | Fraden | |
| 4,799,479 A | 1/1989 | Spears | |
| 4,841,981 A | 6/1989 | Tanabe et al. | |
| 4,862,887 A | 9/1989 | Weber et al. | |
| 4,986,671 A | 1/1991 | Sun et al. | |
| 4,995,398 A | 2/1991 | Turnidge | |
| 5,000,185 A | 3/1991 | Yock | |
| 5,046,501 A | 9/1991 | Crilly | |
| 5,057,105 A | 10/1991 | Malone et al. | |
| 5,106,387 A * | 4/1992 | Kittrell et al. | 606/15 |
| 5,109,859 A | 5/1992 | Jenkins | |
| 5,174,299 A | 12/1992 | Nelson | |
| 5,197,470 A | 3/1993 | Helfer et al. | |
| 5,217,456 A | 6/1993 | Narciso, Jr. | |
| 5,237,996 A | 8/1993 | Waldman et al. | |
| 5,275,594 A | 1/1994 | Baker et al. | |
| 5,279,565 A | 1/1994 | Klein et al. | |
| 5,282,813 A | 2/1994 | Redha | |
| 5,293,872 A | 3/1994 | Alfano et al. | |
| 5,304,173 A | 4/1994 | Kittrell et al. | |
| 5,313,949 A | 5/1994 | Yock | |
| 5,336,178 A | 8/1994 | Kaplan et al. | |
| 5,355,880 A | 10/1994 | Thomas et al. | |
| 5,373,849 A | 12/1994 | Maroney et al. | |
| 5,400,788 A | 3/1995 | Dias et al. | |
| 5,419,767 A | 5/1995 | Eggers et al. | |
| 5,439,000 A | 8/1995 | Gunderson et al. | |
| 5,445,157 A | 8/1995 | Adachi et al. | |
| 5,453,448 A | 9/1995 | Narciso, Jr. | |
| 5,496,271 A | 3/1996 | Burton | |
| 5,541,296 A | 7/1996 | Berman et al. | |
| 5,542,915 A | 8/1996 | Edwards et al. | |
| 5,547,472 A | 8/1996 | Ohishi et al. | |
| 5,558,093 A | 9/1996 | Pomeranz | |
| 5,582,170 A | 12/1996 | Soller | |
| 5,596,995 A | 1/1997 | Sherman et al. | |
| 5,606,974 A | 3/1997 | Castellano et al. | |
| 5,611,338 A | 3/1997 | Gallup et al. | |
| 5,620,438 A | 4/1997 | Amplatz et al. | |
| 5,623,940 A | 4/1997 | Daikuzono | |
| 5,682,899 A | 11/1997 | Nashet et al. | |
| 5,708,275 A | 1/1998 | Rhodes et al. | |
| 5,733,739 A | 3/1998 | Zakin et al. | |
| 5,792,050 A | 8/1998 | Alam | |
| 5,849,028 A | 12/1998 | Chen | |
| 5,871,449 A * | 2/1999 | Brown | 600/474 |
| 5,924,997 A | 7/1999 | Campbell | |
| 5,935,075 A * | 8/1999 | Casscells et al. | 600/474 |
| 6,615,071 B1 * | 9/2003 | Casscells et al. | 600/474 |

FOREIGN PATENT DOCUMENTS

| | | |
|---|---|---|
| EP | 0856278 | 12/1997 |
| EP | 1025797 | 9/1999 |
| GR | 649410 | 1/1976 |
| WO | 8911311 | 11/1989 |
| WO | 9415529 | 7/1994 |
| WO | 9502362 | 1/1995 |
| WO | 9710748 | 3/1997 |

OTHER PUBLICATIONS

Zhang, S. et al. App. Spectrosc 52:400-406 (1998).
Alam, M.K. et al. Appl. Spectrosc 52:393-399 (1998).
Belli, James A., et al. Influence of Temperature on the Radiation Response of Mammalian Cells in Tissue Culture, Radiation Research, 18, 272-276 (1963).
Bellocq et al. J. Biol Chem 273:5086-5092 (1998).
Berliner, Judith A., et al. Atherosclerosis: Basic Mechanisms—Oxidation, Inflammation, and Genetics, Circulation, vol. 91, No. 9, May 1, 1995, pp. 2488-2496.
Biffl, Walter L., et al. Interleukin-6 Delays Neutrophil Apoptosis, Arch Surg/vol. 131, Jan. 1996, pp. 24-30.
Blackburn, M.J., et al. The Sensitivity to Hyperthermia of Human Granuloctye/Macrophage Progenitor Cells (CFU-GM) Derived from Blood or Marrow of Normal Subjects and Patients with Chronic Granulocytic Leukemia, Br.J. Cancer (1984), 50, 745-751.
Buja et al., Role of Inflammation in Coronary Plaque Disruption, pp. 503-505, Circulation, vol. 89, No. 1, Jan. 1994.
Carney et al. Anal Chem 65:1305-13 (1993).
Casscells et al, Thermal Detection of Cellular Infiltrates In Living Artherosclerotic Plaques: Possible Implications for Plaque Rupture and Thrombosis, pp. 1447-1449 and 1422, The Lancet, vol. 347, May 25, 1996.
Cassis et al. Ana Chem 65:1247-56 (1993).
Chen, Ben D0M., et al. Induction of Prostaglandin Production by Hyperthermia in Murine Peritoneal Exudate Macrophages, Cancer Research 47, 11-15, Jan. 1, 1987.
De Vries et al. (FASEB J 12:111-118 (1998).
Dempsey et al. Anne NY Acad Sci 820:149-69 (1997).
Elkon, David, et al. Thermal Inactivation Energy of Granulocyte-Monocyte Stem Cells, Radiation Research 87, 368-372 (1981).
Ensor, Jeffrey E., et al. Warming Macrophages to Febrile Range Destablizes Tumor Necrosis Factor α mRNA Without Inducing Heat Shock, pp. C1140-C1146, (1195). Am. J. Physiol 269: C1140-C1146.
Falk, et al., Coronary Plaque Disruption, pp. 657-671, Circulation, vol. 92, No. 3, Aug. 1, 1995.
Field, S.B., et al. The Relationship Between Heating Time and Temperature: Its Relevance to clinical Hyperthermia, Radiotherapy, and Oncology, 1 (1983) 179-186.
Fouqueray, Bruno, et al. Heat Shock Prevents Lipopolysaccharide-Induced Tumor Necrosis Factor- α Synthesis by Rate Mononuclear Phagocytes, Eur. J. Immunol. 1992, 22:2983-2987.
Gerwick, Leo e., et al. Influence of Nutrient on Energy Deprivation on Cellular Response to Single and Fractionated Heat Treatments, Radiation Research 99, 573-581 (1984).
Gronholdt et al. Eur Heart J. 19 Supp C:C24-C29 (1998).
Hamilton, Raymond F., et al. Blemycin Induces Apoptosis in Human Alveolar Machrophages, Am. J. Physiol 269:L318-L325, 1995.
Haveman, J., et al. The Role of Energy in Hyperthermia-Induced Mammalian Cell Inactivation: A Study Of the Effects of Glucose Starvation and NA Uncoupler of Oxidative Phosphorylayion, Journal of Cellular Physiology 107: 234-241 (1981).
Kim, Young-Myeong, et al. Nitric Oxide Protects Cultured Ray Hepatocytes from Tumor Necrosis Factor-α-Induced Apoptosis by Inducing Heat Shock Protein 70 Expression, vol. 272. No. 2. Issue of Jan. 10, pp. 1402-1411, (1997).
Kobayashi, Eiji, et al. Cell Cycle-Dependent Heat Sensitization of Murine Granulocyte-Macrophage Progenitor Cells in Regenerating Marrow, Cancer Research 45, 1459-1463, Apr. 1985.
Kunkel, S.L., et al., Regulation of Macrophage Tumor Necrosis Factor Production by Prostaglandin $E_2$ Biochemical and Biophysical Research Communication, vol. 137, No. 1., May 29, 1986, pp. 404-410.

Lippman Exp Geron 20:1-5 (1985).

Liu Biochim Biophys Acta 1315:73-77 (1996).

Lodder, R.A., et al. [lodder @pop.uky.edu] "Near-Infrared Spectrometric Imaging in Stroke Research" [http://Kerouac.pharm.uky.edu/ASRG/PittCon/RAL1995/ROBPIT].

Mangan, Dennis F., Lipopolysaccharide, Tumor necrosis Factor -α, and IL-1β Prevent Programmed Cell Death (Apoptosis) in Human Peripheral Blood Monocytes, The Journal of Immunology, vol. 146, 1541-1546, No. 5, Mar. 1, 1991.

Morange, M., et al. Interferon Pretreatment Lowers the Threshold for Maximal Heat-Shock Response in Mouse-Cells, Journal of Cellular Physiology, 127:417-422 (1986).

McShane et al. Appl. Spectrosc 52:1073-1078.

Muller et al., Triggers, Acute Risk Factors and Vulnerable Plaques: the Lexicon of a New Frontier, pp. 809-813, JACC, vol. 23, No. 3, Mar. 1, 1994.

Nagata, Shigekazu et al. The Fas Death Factor, Science, vol. 267, Mar. 10, 1995, pp. 1449-1456.

Nishinia, Hiroshi, et al. Stress0Signalling Kinase Sek 1 Protects Thymocytes From Apoptosis Medicated by CD95 and CD3, Nature, vol. 385, Jan. 23, 1997, pp. 350-353.

Ohdan et al. Transplantation 57:1674-1677 (1994).

Ohdan et al. Transplantation 60:531-535 (1995).

Papadimitriou, J.M., et al. Quantitative Investigations of Apoptosis of Murine Mononuclear Phagocytes During Mild Hyperthermia, Experimental and Molecular Pathology 59, 1-12 (1993).

Patterson et al. FEBS Lett 434:317-321 (1998).

Pizurki, Lara, et al. CAMP Modulated Stress Protein Synthesis in Human Monocytes, Macrophages, Journal of Cellular Physiology, 161:169-177 (1994).

Prins, Johannes B., et al. Apoptosis of Human Adipocytes in Vitro, Biochemical and Biophysical Research Communications, vol. 210, No. 2, (1994), pp. 500-507.

Reddy, M. Venkata, et al. Heat Shock Treatment of Macrophages Causes Increased Release of Superoxide Anion, Infection and Immunity, Jun. 1992, vol. 60, No. 6, pp. 2386-2390.

Ribeiro, Sergio P., et al. Effects of the Stress Response in Septic Rats and LPS-Stimulated Alveolar Macrophages: Evidence for the TNF-α Posttranslational Regulation, Am J Respir Crit Car Med 1996: 154: 1843-1850.

Robinson, M.R. et al. Clin Chem 38:1618-1622 (1992).

Sivo, Judit et al, Heat Shock Mimics Glucocorticoid Effect on IFN-γ- Induced FcγRI and Ia Messenger RNA Expression in Mouse Peritoneal Macrophages, the Journal of Immunology, 1996, pp. 3450-3454.

Snyder, Yvonne M., et al. Transcriptional Inhibition of Endotozin-Induced Monokine Synthesis Following Heat Shock in Murine Peritoneal Macrophages, Journal of Leukocyte Biology, vol. 51, Feb. 1992, pp. 181-187.

Thompson, Craig B. Apoptosis in the Pathogenesis and Treatment of Disease, Science, vol. 267, Mar. 10, 1995, pp. 1456-1462.

Van der Wal et al., Site of Intimal Rupture of Erosion of Thrombosed Coronary Atherosclerotic Plaques: Is Characterized by an Inflammatory Process Irrespective of the Dominant Plaque Morphology, pp. 36-44, Circulation, vol. 89, No. 1, Jan. 1994.

Vaux, D.L., et al. The Molecular Biology of Apoptosis, Proc. Natl. Acad. Sci. USA, vol. 93, pp. 2239-2244, Mar. 1996.

Verheji, Marcel, et al. Requirement for Cereamide-Initiated SAPK/JNK Signaling in Stress-Induced Apoptosis, Nature, vol. 380, Mar. 1996, pp. 75-79.

Wang, Jiang Huai, et al. Induction of Heat Shock Protein 72 Prevents Neutrophil-Mediated Human Endothelial Cell Necrosis, Arch Surg/vol. 130, Dec. 1995, pp. 1260-1265.

Wang, Jiang Huai, el al. Induction of Human Endothelial Cell Apoptosis Requires Both Heat Shock and Oxidative Stress Responses, AM. J. Physiol. 272, 1997, pp. C1543-C1551.

Westra, Arthur, et al. Variation in Sensitivity to Heat Shock During the Cell-Cycle of Chinese hamster Cells in Vitro, Int. J. Radiant. Biol., 1971, vol. 19, No. 5, pp. 467-477.

* cited by examiner

METHOD OF DETECTING VULNERABLE ATHEROSCLEROTIC PLAQUE

CROSS-REFERENCE TO RELATED APPLICATIONS

The present application is a continuation application of Ser. No. 09/268,609 filed Mar. 15, 1999 now U.S. Pat. No. 6,475,159, which is a divisional application of U.S. patent application Ser. No. 08/717,449, filed on Sep. 20, 1996, now U.S. Pat. No. 5,935,075, which claims the benefit of 35 USC 111(b) provisional application Ser. No. 60/004,061, filed Sep. 20, 1995, and entitled "Catheters and Methods Detecting Thermal Discrepancies in Blood Vessels.

BACKGROUND OF THE INVENTION

This invention was made with government support under Grant No. 91HL07 awarded by the National Heart Lung and Blood Institute, giving the federal government certain rights in the invention. In addition, the invention described herein was made in the performance of work under a NASA contract and is subject to the provisions of Section 305 of the National Aeronautics and Space Act of 1958, Public Law 85-568 (72 Stat. 435; 42 U.S.C. 2457).

A. Field of the Invention

This invention relates to the medical diagnosis and treatment of arterial disease by means of temperature differential sensing, and particularly, infrared-sensing with devices such as temperature probes, cameras, and catheters. In particular, the invention provides catheters and methods of using catheters to diagnose arterial diseases detectable by thermal discrepancies in the arterial wall.

B. Description of the Related Art

Problems in Diagnosis

Plaque Physiology

Atherosclerotic coronary artery disease is the leading cause of death in industrialized countries. An atherosclerotic-plaque is a thickened area in the wall of an artery. Typically, patients who have died of coronary disease may exhibit as many as several dozen atherosclerotic plaques; however, in most instances of myocardial infarction, cardiac arrest, or stroke, it is found that only one of these potential obstructions has, in fact, ruptured, fissured, or ulcerated. The rupture, fissure, or ulcer causes a large thrombus (blood clot) to form on the inside of the artery, which may completely occlude the flow of blood through the artery, thereby injuring the heart or brain. A major prognostic and diagnostic dilemma for the cardiologist is how to predict which placque is about to rupture.

Most ruptured plaques are characterized by a large pool of cholesterol or necrotic debris and a thin fibrous cap with a dense infiltration of macrophages. The release of matrix-digesting enzymes by the cells is thought to contribute to plaque rupture. Other thromboses are found on non-ruptured but inflamed plaque surfaces.

Inflammation in an arterial plaque is the result of a series of biochemical and mechanical chancres in the arterial wall. Plaque, a thickening, in the arterial vessel wall results from the accumulation of cholesterol, proliferation of smooth muscle cells, secretion of a collagenous extracellular matrix by the cells, and accumulation of macrophages and, eventually, hemorrhage (bleeding), thrombosis (clotting) and calcification. The consensus theory is that atherosclerotic plaque develops as a result of irritation or biochemical damage of the endothelial cells.

The endothelial cells which line the interior of the vessel prevent inappropriate formation of blood clots and, inhibit contraction and proliferation of the underlying smooth muscle cells. Most investigators believe that atherosclerotic plaques can develop when endothelial cells are damaged or dysfunctional. Dysfunction in endothelial cells is typically produced as a result of injury by cigarette smoke, high serum cholesterol (especially oxidized low density lipoprotein), hemodynamic alterations (such as those found at vessel branch points), some viruses (herpes simplex, cytomegalovirus) or bacteria (e.g., *Chlamydia*), hypertension, some hormonal factors in the plasma (including angiotension II, norepinephrine), and other factors as yet unknown. As a result of these gradual injuries to the endothelial cells, an atherosclerotic plaque may grow slowly over many years. However, it is now well documented that if a plaque ruptures, it often grows abruptly.

When plaque rupture develops, there is hemorrhage into the plaque through the fissure where the surface of the plaque meets the bloodstream. Blood coagulates (forms a thrombus) quickly upon contact with the collagen and lipid of the plaque. This blood clot may then grow to completely occlude the vessel or it may remain only partially occlusive. In the latter case, the new clot quite commonly becomes incorporated into the wall of the plaque, creating a larger plaque.

Plaques at Risk of Rupturing

Considerable evidence indicates that plaque rupture triggers 60% to 70% of fatal myocardial infarctions and that monocyte-macrophages contribute to rupture by releasing metalloproteinases (e.g., collagenases, stromelysin) which can degrade and thereby weaken the overly fibrous cap. Van der Wal, et al., *Circulation* 89:36–44 (1994); Nikkei, et al., *Circulation* 92:1393–1398 (1995); Falk, et al., *Circulation* 92:2033–20335 (1995); Shah, et al., *Circulation* 244 (1995); Davies, et al., *Br Heart J* 53:363–373 (1985); Constantinides, *J Atheroscler Res* 6:1–17 (1966). In another 25% to 30% of fatal infarctions, the plaque does not rupture, but beneath the thrombus the endothelium is replaced by monocytes and inflammatory cells. Van der Wal, et al., *Circulation* 89:36–44 (1994); Farb, et al., *Circulation* 92:1701–1709 (1995). These cells may both respond to and aggravate intimal injury, promoting thrombosis and vasoconstriction. Baju, et al., *Circulation* 89:503–505 (1994).

Unfortunately, neither plaque rupture nor plaque erosion is predicable by clinical means. Soluble markers (P-selectin, von Willebrand factor, angiotensen-converting enzyme, C-reactive protein, D-dimer; Ikeda, et al., *Circulation* 92:1693–1696 (1995); Merlini, et al., *Circulation* 90:61–8 (1994); Berk, et al., *Am J Cardiol* 65:168–172 (1990)) and activated circulating inflammatory cells are found in patients with unstable angina pectoris, but it is not yet known whether these substances predict infarction or death. Mazzone, et al., *Circulation* 88:358–363 (1993). It is known, however, that the presence of such substances cannot be used to locate the involved lesion.

Low-shear regions opposite flow dividers are more likely to develop atherosclerosis, (Ku, et al., *Arteriosclerosis* 5:292–302 (1985)), but most patients who develop acute myocardial infarction or sudden cardiac death have not had prior symptoms, much less an angiogram. Farb, et al., *Circulation* 92:1701–1709 (1995).

Certain angiographic data has revealed that an irregular plaque profile is a fairly specific, though insensitive, indicator of thrombosis. Kaski, et al., *Circulation* 92:2058–2065 (1995). These stenoses are likely to progress to complete occlusion, while less severe stenoses are equally likely to progress, but less often to the point of complete occlusion. Aldeman, et al., *J Am Coll Cardiol* 22:1141–1154 (1993). However, because hemodynamically nonsignificant stenoses more numerous than critical stenoses and have not triggered collateral development, those which do abruptly occlude actually account for most myocardial infarctions. Ambrose, et al., *J Am Coll Cardiol* 12:56–62 (1988); Little, et al., *Circulation* 78: 1157–1166 (1988).

Moreover, in postmortem studies, most occlusive thrombi are found over a ruptured or ulcerated plaque that is estimated to have produced a stenosis of less than 50% in diameter. Shah, et al., *Circulation* 244 (1995). Such stenoses are not likely to cause angina or a positive treadmill test. (In fact, most patients who die of myocardial infarction do not have three-vessel disease or severe left ventricular dysfunction.) Farb, et al., *Circulation* 92:1701–1709 (1995).

In the vast majority of plaques causing a stenosis less than or equal to 50%, the surface outline is uniform, but the deep structure is highly variable and does not correlate directly with either the size of the plaque or the severity of the stenosis. Pasterkamp, et al., *Circulation* 91:1444–1449 (1995); Mann and Davies *Circulation* 94:928–931 (1996).

Certain studies have been conducted to determine the ability to identify plaques likely to rupture using intracoronary ultrasound. It is known that (1) angiography underestimates the extent of coronary atherosclerosis, (2) high echo-density usually indicates dense fibrous tissue, (3) low echo-density is a feature of hemorrhage, thrombosis, or cholesterol, and (4) shadowing indicates calcification. Yock, et al., *Cardio* 11–14 (1994); McPerhson, et al., *N Engl J Med* 316:304–309 (1987). However, recent studies indicate that intra-vascular ultrasound technology currently cannot discriminate between table and unstable plaque. De Feyter, et al., *Circulation* 92:1408–1413 (1995).

The rupture process is not completely understood, but it is known that the plaques most likely to rupture are those that have both a thin collagen cap (fibrous scar) and a point of physical weakness in the underlying plaque. It is known that plaques with inflamed surfaces or a high density of activated macrophages and a thin overlying cap are at risk of thrombosis. Van der Wal, et al., *Circulation* 89:36–44 (1994), Shah, et al., *Circulation* 244 (1995); Davies, et al., *Br Heart J* 53:363–373 (1985); Farb, et al., *Circulation* 92:1701–1709 (1995); Van Damme, et al., *Cardiovasc Pathol* 3:9–17 (1994). Such points are thought to be located (as determined by modeling studies and pathologic analysis) at junctures where pools of cholesterol meet a more cellular and fibrous part of the plaque. Typically, macrophages (inflammatory cells), which produce heat, have been found at these junctures. Since these inflammatory cells release enzymes capable of degrading the collagen and other components of the extracellular matrix, it is thought that they are crucial to the process-of plaque rupture or fissuring.

Transplant Vasculopathy

Inflammation also plays an important role in the rejection of transplanted organs, a process which begins by an attack of host T lymphocytes in the grafted donor organ's endothelial cells. Yeung et al. *J. Heart Lung Transplant.* 14:S215–220 (1995); Pucci et al. *J. Heart Transplant.* 9:339–45 (1990); Crisp et al. *J. Heart Lung Transplant.* 13:1381–1392 (1994). Recruitment and proliferation of inflammatory and smooth muscle cells are heat-generating processes, whose effects are detectable in advance of the detection of vessel narrowing using stress tests, ultrasound, or angiography. Johnson et al. *J. Am. Coll. Cardiol.* 17: 449–57 (191); St. Goar et al. *Circulation* 85:979–987 (1992). In addition to the host attack of "non-self" antigens of the donor organs, many transplanted tissues develop cytomegalovirus infections, an event that is also heat-generating. Grattan et al. *JAMA* 261:3561–3566 (1989). These events in transplant physiology are ones for which it would be valuable to track in patients recovering from much surgery.

Restenosis

Another serious problem in diagnostic cardiology is restenosis, a renarrowing of an artery that has undergone one or more interventional techniques to relieve an original stenosis (caused by plaque). Such techniques include balloon angioplasty, atherectomy (shaving or cutting the plaque), and laser angioplasty. Balloon angioplasty of the coronary arteries is a major advance in treatment and has been performed on hemodynamically significant coronary stenoses (those that are 70% to 99%, of the cross-sectional diameter of the vessel) with a success rate of 90%. In about 40% Of the patients, however, restenosis occurs in the vessel and most of the benefit gained by the procedure is lost. Thus, another major diagnostic and prognostic dilemma for cardiologists not readily addressed by prior art devices or methods is predicting which patients will develop restenosis.

Restenosis may occur when the removal of plaque by angioplasty or atherectomy injures the artery wall. The injury to the vessel wall causes the smooth muscle cells at that site to proliferate and to secrete an extracellular matrix which again narrows the artery. Both cell proliferation and secretion are exergonic (heat-generating) processes. Additionally, it is known that macrophage concentration in a vessel is correlated to the risk of restenosis.

Many factors have been reported to predict which patients will develop restenosis. However, these studies are markedly at odds with each other and no factor has been strongly predictive of the restenosis process. Thus, cigarette smoking, hypertension, hypercholesterolemia, unstable angina, age, sex, and many other factors have been only weakly predictive, at best.

Prior Art Devices/Methods

A number of approaches and devices have been proposed to diagnose or treat vascular obstructions. U.S. Pat. No. 3,866,599 relates to a fiberoptic catheter for insertion into the cardiovascular system for the measurement of oxygen in blood. For the purpose of detecting oxygenation levels in the blood, optical fibers are used to first project infra-red and red light at the catheter tip into the blood. The infra-red and red light reflected by the blood is then returned through the optical fibers to an oximeter. The ratio of infra-red light reflected to that absorbed by the blood is proportional to the oxygen saturation in the blood. This catheter design is also one wherein there is at the distal end of the element a recess preventing the ends of the fibers from contacting the vessel wall and an exterior sleeve which can be expanded to further space the fibers from the wall of the vessel. However, the fiberoptic catheter of this patent does not permit detection of heat.

In some prior art devices, temperature sensing elements have been used. U.S. Pat. No. 4,752,141 relates to fiberoptic sensing of temperature and/or other physical parameters using a system comprising (1) an optical fiber (2) means including a source of visible or near visible electromagnetic radiation pulses at one end of the fiber for directing the radiation along the fiber to another end of the fiber (3) a sensor positioned at or near the end of the fiber in a manner to receive the radiation, modulate it by the temperature, and redirect the modulated radiation back through the optical fiber to the sensor (4) the sensor comprising at least one optical element in the path of the source of radiation whose optical properties vary in response to the magnitude of temperature changes and (5) means positioned at the end of the fiber receiving the modulated radiation for measuring a function related to the time of the resulting luminescent radiation intensity decay after an excitation pulse indicating the temperature of the sensor. These temperature sensors were designed to physically contact a surface and were built with an elastomeric substance at the end of the fiber to which a thin layer of phosphor material had been deposited. The phosphor reacts to the temperature and emits radiation which travels up the fiber and is detected by the sensor. Contact temperature determinations require the ability of the catheter to be placed in contact with the locus whose temperature is to be measured.

U.S. Pat. No. 4,986,671 relates to a fiber optic probe with a single sensor formed by a elastomeric lens coated with a light reflective and temperature dependent material over which is coated a layer of material that is absorptive of infrared radiation thereby allowing a determination of characteristics of heat or heat transfer. One application is in a catheter for providing pressure, flow and temperature of the blood in a blood vessel.

Other methods utilizing differing means for heat detection are known. The sensitivity and/or toxicity of these devices is unknown. U.S. Pat. No. 4,140,393 relates to the use of birefringement material as a temperature probe. U.S. Pat. No. 4,136,566 suggests the use of the temperature dependent light absorption characteristics of gallium arsenide for a temperature sensor. U.S. Pat. No. 4,179,927 relates to a gaseous material having a temperature dependent light absorption.

Other approaches utilize excitation techniques to detect heat. U.S. Pat. No. 4,075,493 relates to the use of a luminescent material as a temperature sensor, exciting radiation of one wavelength range being passed along the optical fiber from the measuring instrument, and temperature dependent luminescent radiation being emitted from the sensor back along the communicating optical fiber for detection and measurement by the instrument. It is the luminescent sensor technology which has found the greatest commercial applicability in fiber optic measurements, primarily for reasons of stability, wide temperature range, ability to minimize the effect of non-temperature light variations, small sensor size and the like.

An example of a luminescent fiberoptic probe that can be used to measure the velocity of fluid flow, among other related parameters, is given in U.S. Pat. No. 4,621,929. Infrared radiation is directed to the sensor along the optical fiber and is absorbed by a layer of material provided for that purpose. Once heated, the sensor is then allowed to be cooled by a flow of fluid, such cooling being measured by the luminescent sensor. The rate of cooling is proportional to the heal transfer characteristics and flow of the surrounding liquid.

U.S. Pat. No. 4,995,398 relates to the use of thermography during the course of by-pass heart surgery for the purpose of checking the success of the operation before closing the chest cavity. This patent describes the use of a scanning thermal camera, image processing, temperature differentials and displaying images in real time. The invention relies on the use of a cold injectate which when it mixes with warmer blood provides images captured on a thermal camera focusing on the heart to detect stenoses at the sites of distal anastomoses.

U.S. Pat. No. 5,046,501 relates to a method of identifying atherosclerotic plaque versus structurally viable tissues using a fluorescent beam at a single excitation wavelength of between 350 and 390 nm preferably from a laser which allows differentiation of these tissues. No catheter was used in the examples of the patent. Thus, in situ imaging is not disclosed or taught by this patent. Moreover, no technique is described by this patent for predicting plaque rupture, restenosis or transplant vasculopathy.

U.S. Pat. No. 5,057,105 relates to a hot tip catheter assembly comprising a heater, a cap, a thermocouple, power leads, and a central distal lumen to position the catheter in the artery. The thermocouple is included to continuously monitor the heating of the catheter tip in order to prevent overheating. The tip when properly placed on a plaque build up, melts the plaque.

U.S. Pat. No. 5,109,859 relates to ultrasound guided laser angioplasty comprising a laser at the tip of a catheter, an ultrasound device also at the tip of the laser for guidance, and a proximal occlusion balloon to provide stabilization and a blood free environment. This patent apparently also relates to estimating the mass of a plaque tissue. There is no teaching that the ultrasound device of the patent can distinguish histological features (i.e., what cells and extracellular matrix are within the plaque). Thus, it is not likely that such a device could be used to predict plaque rupture. Indeed, recent studies have found that intravascular ultrasound cannot identify which plaques are at risk of rupturing. de Feytia *Circulation* 92:1408–13 (1995).

U.S. Pat. No. 5,217,456 relates to an intra-vascular guidewire-compatible catheter which has a source of illumination and a synchronous fluorescence detector. Light in a wavelength that induces fluorescence in tissues emanates radially from an aperture on the side of the catheter. Fluorescence emitted from the tissues enters the catheter through the same aperture and is conveyed to a spectral analyzer. This information can be used to differentiate healthy tissue from atherosclerotic plaque. However, this device does not distinguish between plaque on the basis of heat differential.

U.S. Pat. No. 5,275,594 relates to methods and apparatus for distinguishing between atherosclerotic plaque and normal tissue by analyzing photoemissions from a target site. The system includes a source of laser energy for stimulation of fluorescence by non-calcified versus calcified atherosclerotic plaque, and an analyzing means for determining whether a spectrum of fluorescence emitted by a tissue represents calcified or non-calcified atherosclerotic plaque at a target site, based upon the time domain signal of calcium photoemission following fluorescent excitation of the calcium. When atherosclerotic plaque is identified, laser energy is used to ablate the plaque.

Prior art approaches to intravascular arterial diagnosis and repair have been numerous yet have failed to provide certain capabilities. In particular, such prior art catheters and methods have failed to provide means for detecting and treating atherosclerotic plaque since they have not been able to differentiate between those plaques at risk of rupturing and occluding and those that are not presently at such risk even if they are capable of determining the presence or absence of calcification of the plaque. Similarly, prior art approaches have not provided effective means for identifying specific arterial sites at risk for arterial restenosis after angioplasty or atherectomy. Prior art approaches have also failed to provide practical and effective means for detecting transplant vasculopathy. Neither have prior art approaches been able to effectively identify patients who have arterial wall areas of lower rather than hither temperature, such as areas of extensive scarring, lipid pools where there is no cellular infiltration, or areas of hemorrhage and thrombosis which have yet to be colonized by inflammatory cells.

SUMMARY OF THE INVENTION

The present invention overcomes at least some of the failures of the prior art by providing an infrared-sensing catheter for detecting heat-producing, inflammatory cells and vessel wall cells, and thus predicting the behavior of injured blood vessels in medical patients. The catheters and methods of the present invention provide effective means for detecting and treating atherosclerotic plaque which is capable of differentiating between, among other pathologies, those plaques at risk of rupturing and occluding and those that are not presently at risk. The catheters and methods of the present invention also provide effective means for identifying specific arterial sites at risk for arterial restenosis after angioplasty or atherectomy, or which patients are at risk due to vasculopathy, or tissue rejection. The catheters and methods of the present invention also are capable of effectively identifying patients who have arterial wall areas of unusually low temperature and which represent previously undetected arterial at-risk areas—just as excess heat can identify regions at risk due to inflammation, sub-normal heat (areas cooler than the rest of a vessel) indicates a lack of actively metabolizing healthy cells (since heat in the body results from actively metabolizing cells). Non-cellular areas are typically regions of hemorrhage, thrombosis, cholesterol pools, or calcium—all indicators of high risk plaques. The invention's devices and methods achieve these ends by identifying and analyzing thermal discrepancies in the wall temperature of blood vessels.

The invention in one regard relates to apparatus for analyzing optical radiation of a vessel. In another regard, the invention relates to methods for analyzing optical radiation, which methods are best preferably achieved using the apparatus of the invention.

Optical radiation of particular interest in the invention is that radiation which falls in the optical spectrum in the wavelength interval from about 2–14 μm. An attractive feature of infrared is its penetration through calcium (relative to white light and ultrasound). Benaron, et al., *J Clin Monit* 11:109–117 (1995).

The vessels of particular interest in the invention are those vessels where the access to a surface of which is problematic. Thus, where the internal diameter of a vessel is too small for ready access by a traditional temperature probe (i.e., a contact thermometer or thermocouple), the apparatus and methods of the invention will find utility. Similarly where the vessel, while of sufficiently large internal diameter for access by a temperature probe, has one or others of its openings narrowed, occluded or otherwise blocked, the apparatus and methods of the invention will find utility. Thus, of particular interest in application of the apparatus and methods of the invention are vessels of the body, including vessels circulating and transporting sera (i.e. blood) such as arteries, veins, sinuses, heart cavities and chambers.

The invention relates to apparatus and methods in which there is at least one optical fiber used which is capable of transmitting optical radiation from a distal end of the fiber, usually inside a vessel, to a proximal end of the fiber, usually outside the vessel. Optical fibers of the invention will exhibit certain key parameters related to their ability to transmit wavelengths in the region of 2–14 μm. These key parameters include optical transparency, flexibility and strength. The optical fibers of the invention are those which may be extruded in ultrathin diameters and which transmit over the appropriate infra-red spectral region. The infrared fiberoptic can be constructed from a variety of substances known to those of skill in the art such as zirconium fluoride ($ZrF_4$), silica, or chalcogenide (AsSeTe). $ZrF_4$ fibers are well suited to the apparatus and methods of the invention because such fibers have >90% transmission capabilities over 1 meter for small diameters.

The optical fibers useful in the apparatus and methods of the invention will also be ones capable of placement proximate to a locus of a wall of the vessel being investigated. This criterion is achieved in part by the flexibility of the fiber optic. In additional part, this criterion is met by the ultrathin nature of the diameter of the fiber optic.

The apparatus and methods of the invention also utilize a balloon which encases a distal end of the fiber. The balloon, in one embodiment, may be one which is transparent to the optical radiation of interest. In that instance, optical radiation originating outside the balloon is transmitted through the outer surface of the balloon to the inner surface of the balloon and on to the entry point for optical radiation into the optical fiber. It is important, in this embodiment, for there to be little if any absorption, reflection or other diversion of the optical radiation emanating from the source (i.e., the vessel wall, a locus such as a plaque locus) during its transmission through the surfaces of the balloon. Such unwanted absorption may be caused by blood or other body fluids. Therefore, transparency for purposes of the invention means an ability to transmit substantially all optical radiation from a particular source through the balloon surfaces to the optical fiber.

It is important, in this embodiment, for there to be substantially total conduction of the heat, while having substantially no loss of the heat emanating from the source (i.e., the vessel wall, a locus such as a plaque locus) as it contacts the outer surface of the balloon. Therefore, opacity (opaque) for purposes of the invention means an ability to absorb substantially all optical radiation from a particular source on the outer balloon surface. Thereafter, the inner surface of the balloon will re-emit a proportional amount of radiation to that absorbed on the outer surface immediately adjacent the locus originating the radiation. This re-emitted radiation will be detectable by the fiber optic system encased inside the balloon.

The apparatus and methods of the invention also utilize a detector capable of detecting a difference in the optical radiation of interest, between the locus and the average optical radiation along the vessel wall being investigated. In certain preferred embodiments, the detector of the invention is one which has a sensitivity capable of detection of differences in infra-red radiation as small as 50° mK., and in the range of 10 to 100° mK.

Where the balloon is one which is transparent to the radiation directly emitted from the locus or from the vessel wall portions outside the specific locus, the detector will be one capable of detecting the radiation which is transmitted through the balloon's outer and inner surfaces. Where the balloon is one which is opaque to the radiation directly emitted from the locus or from the vessel wall portions outside the specific locus, the detector will be one capable of detecting the radiation which is re-emitted from the balloon's inner surface opposite the balloon's outer surface which is directly in contact with the locus.

In preferred embodiments the apparatus and methods of the invention will rely on detection of optical radiation in the infra-red radiation ranges. In particular, as noted above, ranges of 2–14 micrometers are of particular interest in the apparatus and methods of the invention. Referring to FIG. 2, it can be seen that it is possible to plot curves for radiation (numbers of photons×1×10$^{17}$) being emitted by black bodies held at differing constant temperatures ($T_1$, $T_2$ and $T_3$ each refer to temperatures in the range of 300–310° K. which vary from one another increasingly by 1° K.) in the wavelength range of 3 up to 6 micrometers. It can also be seen in the inset to FIG. 2, that in the range of approximately 5.3 to 5.6 micrometers, black bodies held at constant temperatures in the range of 300–310° K. and differing from one another by only a single degree, appear as easily distinguishable curve segments, emitting photons from these black bodies in the range of approximately 0.21×10$^{17}$ to 0.40×10$^{17}$ photons. Thus, it is preferred to select a wavelength for sampling the radiation from the wall and specific locus on the wall of a vessel which will provide similarly distinguishable curves.

In certain preferred embodiments, the apparatus and methods of the invention may comprise at least two fibers, although the use of greater than two fibers is clearly possible where merited, such as when detection along the axis of the vessel is preferred at greater than a single position simultaneously. In other preferred embodiments, where at least two fibers are utilized, at least one of the fibers is a reference fiber and another of the fibers is a signal fiber. The signal fiber is a fiber designed to transmit all optical radiation focused into its length from its distal end to its proximal end. Conversely, the reference fiber is a fiber which is used as a control against which the signal fiber transmissions may be compared. Thus, where optical radiation exiting the proximal end of the signal fiber is compared to that exiting the proximal end of the reference fiber, a determination can be readily made as to relative amounts of optical radiation exiting the signal fiber which is due to other than optical radiation emitted by the locus interest.

The apparatus of the invention may also be optically connected at the distal end of the signal fiber to an optically reflective surface capable of directing optical radiation arising radially to said distal end, and on into said fiber. U.S. patent application Ser. No. 08/434,477 in which certain of the present inventors are named co-inventors, and which is incorporated herein by reference, describes such an optically reflective surface. As opposed to the signal fiber, the reference fiber will typically be coated on its distal end with a material that substantially prevents optical radiation from entering it.

The apparatus of the invention is also one in which the inner surface of the opaque occluding balloon emits a black body spectrum modulated by the transmission spectrum of the balloon. The balloon, upon inflation, will substantially limit flow of fluids within the vessel. The flow limitation required is one in which only so much flow occurs as will not cause a rise or fall in average background IR radiation along the vessel wall immediately distal the inflated balloon. In addition, in preferred embodiments, the apparatus of the invention is one where the balloon, upon inflation, substantially excludes the presence of intervesicular fluids between the fibers inside the balloon and the wall of the vessel most proximate to the test locus.

In use, the apparatus of the invention will be placed along an axis of the vessel. in this manner, it will be possible to bring the diagnostic fiber array into close proximity with a locus to be diagnosed. In certain preferred embodiments, the locus will be one which contains plaque. In particular, the apparatus as previously noted will be useful in detecting among those plaques with which it is brought into proximity, whether a given plaque is one at risk of rupturing. In most instances, the apparatus of the invention will be used to diagnose thermal discrepancies on the interior wall of a vessel.

The apparatus of the invention is in its most preferred embodiments a catheter. Typical of catheters used inside of blood vessels, the catheter of the invention will be one designed for use with a guidewire. The guidewire will allow optional removal and reinsertion at the discretion of the surgeon, for example where after diagnosing a plaque at risk of rupturing using the catheter of the invention, the surgeon may wish to brine another diagnostic device or a therapeutic device such as a laser into the same position next to the problematic plaque.

The apparatus of the invention is also one where the detector is preferably optically connected to a proximal end of the fiber, and if there is more than one fiber, to a proximal end of each of the fibers. In preferred embodiments, the detector will be a multi-wavelength radiometer.

Such a radiometer will preferably be a spinning circular variable filter whose transmission wavelength is a function of its angle of rotation. In such a filter, it is possible to prevent transmission of all but a narrow band of wavelengths of light by adjusting the rotational angle. Said differently, such a filter can be made to be transparent to highly selected wavelengths by its rotational characteristics. Thus, in certain embodiments, the filter will be one transparent to radiation with a wavelength of approximately between 2 to 6 micrometers. In highly preferred embodiments, the filter will be transparent to radiation with a wavelength of approximately 3 micrometers.

One of the keys to this invention as it relates to the apparatus, is that it automatically provides a reference for each spectrum by sampling approximately 3 $\mu$m. For the range of temperatures expected in biological organisms, 300–310° K., the blackbody spectrum at this wavelength is essentially the same. This provides a zero for each signal and locks down the low wavelength side of the signal. Without this, there would be no way to fit a signal to a blackbody spectrum since-the vertical scale would be "unfixed".

Where the apparatus of the invention utilizes the transmitted information from more than one fiber through a filter for comparative purposes, it will be preferred to utilize an offset in the distal fiber ends. Thus, where the distal ends of the signal fiber and the reference fiber are offset from one another, the offset will be at a distance sufficient to allow sampling of radiation emitted from either fiber to pass the filter-at a substantially identical location on the filter.

The apparatus of the invention when used in conjunction with a radiometer, will preferably be one optically connected to at least one photoelectric device capable of converting the transmitted radiation into an electrical signal. The photoelectric device is preferably one electrically connected to a device capable of digitizing the electrical signal (a digitizer).

Once the apparatus of the invention has created a digitized signal, the digitized signal is mathematically fitted to a curve selected from a spectrum of curves for black bodies held at temperatures between approximately 300–310° K. The curves of the controlled black bodies are those plotted as numbers of photons emitted from each black body for each wavelengths. In instances where such a digitized signal is to be used to diagnose thermal discrepancies in the interior wall of a blood vessel, the particular selection of black body control curves will be made with the knowledge of typical temperatures of the human body.

Thus, in a preferred embodiment, the apparatus of the invention will be a catheter for analyzing infra-red radiation of a blood vessel. Such a preferred device will comprise at least two fibers capable of transmitting the radiation and capable of placement along an axis of the vessel proximate to a plaque-containing locus of an interior wall of the vessel. At least one of the fibers will be a reference fiber coated on its distal end with a material that substantially prevents optical radiation from entering it, and at least one of the other of the fibers will be a signal fiber whose distal end is optically connected to an optically reflective surface capable of directing optical radiation arising radially to its distal end into and along its shaft. Such a preferred device will also have a balloon encasing the distal ends of each of the fibers, which balloon upon inflation will substantially limit the flow of fluids within the blood vessel. In addition, the balloon will substantially exclude fluids between the fibers and the wall of the vessel most proximate to the locus to be tested. The balloon will be transparent to or opaque to the radiation arising inside the vessel and will have an inner surface exhibiting spatially constant optical radiation emissivity. This inner surface of the opaque balloon will be one which emits a black body spectrum. The catheter will be one having a guidewire. It will also have a detector, optically connected to a proximal end of each of the fibers, and capable of detecting a difference in the radiation between the locus and average optical radiation along the wall of the vessel. The detector will further comprise a multi-wavelength radiometer with a spinning circular variable filter, the filter being such that its transmission wavelength is a function of its angle of rotation. The distal ends of the fibers will be offset from one another a distance sufficient to allow sampling of radiation emitted from either fiber to pass the filter at a substantially identical position on the filter. Further, the radiometer will be optically connected to at least one photoelectric device capable of converting the transmitted and filtered radiation into an electrical signal, which signal is capable of being digitized, and which digitized signal is mathematically fitted to a curve selected from a spectrum of curves for black bodies held at temperatures between approximately 300–310° K., where the curves are plotted as numbers of photons emitted from each of the black bodies for each of the wavelengths.

The invention also relates to an analytical method, suitable in certain embodiments for diagnosing medical conditions. Thus, the invention relates to a method for analyzing optical radiation of a locus in a vessel wall. The method of the invention comprises placing at least one optical fiber capable of transmitting radiation proximate to the locus. In preferred embodiments, the placement of the fiber and balloon is accomplished by catheterization. Either prior to or after placement proximate to the locus to be analyzed, a balloon encasing a distal end of the fiber is inflated within the vessel to cause the balloon to limit flow of fluids within the vessel. As previously detailed, the balloon is transparent to or opaque to the thermal radiation and has an inner surface exhibiting spatially constant optical radiation emissivity. The methods of the invention further call for transmitting the radiation along the fiber to a detector capable of detecting a difference in the radiation between the locus and the average optical radiation along the vessel wall.

More specifically, the invention relates to a method of detecting plaque at risk of rupturing along a blood vessel. This preferred method comprises inserting a guidewire into the blood vessel to be diagnosed and then catheterizing the vessel along the guidewire with at least two fibers capable of transmitting infra-red radiation along an axis of the vessel proximate to a plaque-containing locus of an interior wall of the vessel. Thereafter, the steps of the method of the invention is carried out as described above.

The invention also relates to a method of surgically treating a patient with a plurality of plaque loci within a vessel. Such a method comprises determining which one or more of the plurality of plaque loci has a temperature elevated above that of the average vessel wall temperature. Once such a determination is made, the surgeon removes or reduces the plaque loci found to have an elevated temperature. This method has as its determination step the methods described above for analyzing optical radiation of plaque locus in a vessel wall. Once plaque at risk is identified, a number of therapies may be used to reduce the risk.

Accordingly, it is an object of the present invention to identify patients who have coronary atherosclerotic plaque at risk of rupture by identifying the specific plaque(s) at risk. Another object of the present invention is to identify patients at risk for arterial restenosis after angioplasty or atherectomy by identifying the specific arterial site(s) at risk. A further object of the present invention is to identify patients at risk of transplant vasculopathy. Another object is to identify patients at risk for stroke, loss of mobility, and other illnesses by identifying sites of potential plaque rupture in the carotid arteries, the intracerebral arteries, the aorta, and the iliac and femoral arteries. Another object of the present invention is to identify patients who have arterial areas of lower rather than higher temperature, such as an area of extensive scarring, a lipid pool with no cellular infiltration, or an area of hemorrhage and thrombosis which has yet to be colonized by inflammatory cells. The delineation of a cholesterol pool is useful in following the regression of plaques. Identifying such areas for follow-up study will localize those likely to be inflamed in the future.

Yet another object of the present invention is to deliver specific local therapy to the injured areas identified by the catheter. These therapies include, but are not limited to, therapies which prevent or limit inflammation (recruitment, attachment, activation, and proliferation of inflammatory cells), smooth muscle cell proliferation, or endothelial cell infection, including antibodies, transforming growth factor-$\beta$ (TGF-$\beta$), nitric oxide (NO), NO synthase, glucocorticoids, interferon gamma, and heparan and heparin sulfate proteoglycans, and the various complementary DNAs that encode them.

The invention's methods and devices will have a number of utilities. Each will reduce morbidity and mortality from coronary and carotid artery atherosclerosis. Each will reduce the incidence of restenosis and thus the need for repeated angioplasties or atherectomies. Each will also reduce the incidence of vasculopathy in organ-transplant patients. In turn, these outcomes will produce the benefits of better health care, improved public health, and reduced health care costs. These and other uses of the present invention will become clearer with the detailed description to follow.

DESCRIPTION OF PREFERRED EMBODIMENTS

The Catheter Embodiment

Figure 1:
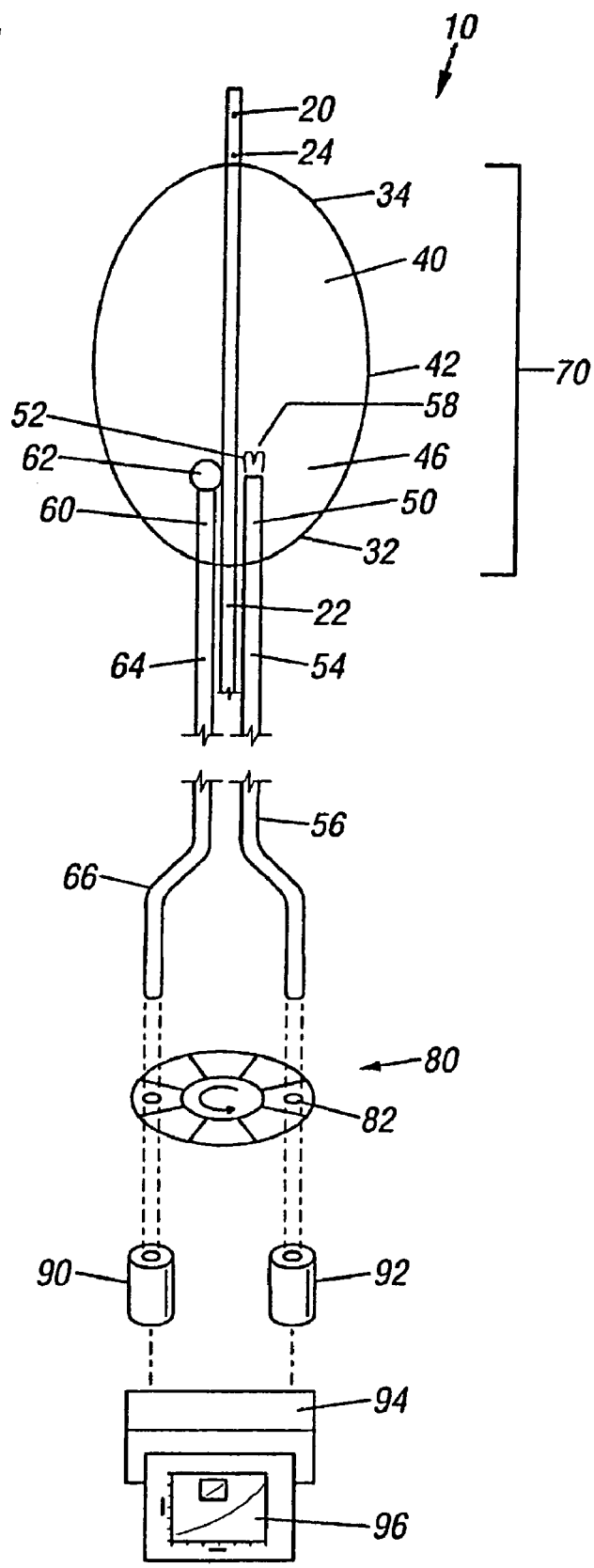
FIG. 1 is a schematic representation of the apparatus of the present invention with its infra-red detection unit at its proximal end and the sensor tipped distal end of the catheter as well as the guide wire disposed within a flexible outer catheter (not shown) which surrounds the optical fibers.
Figure 2:
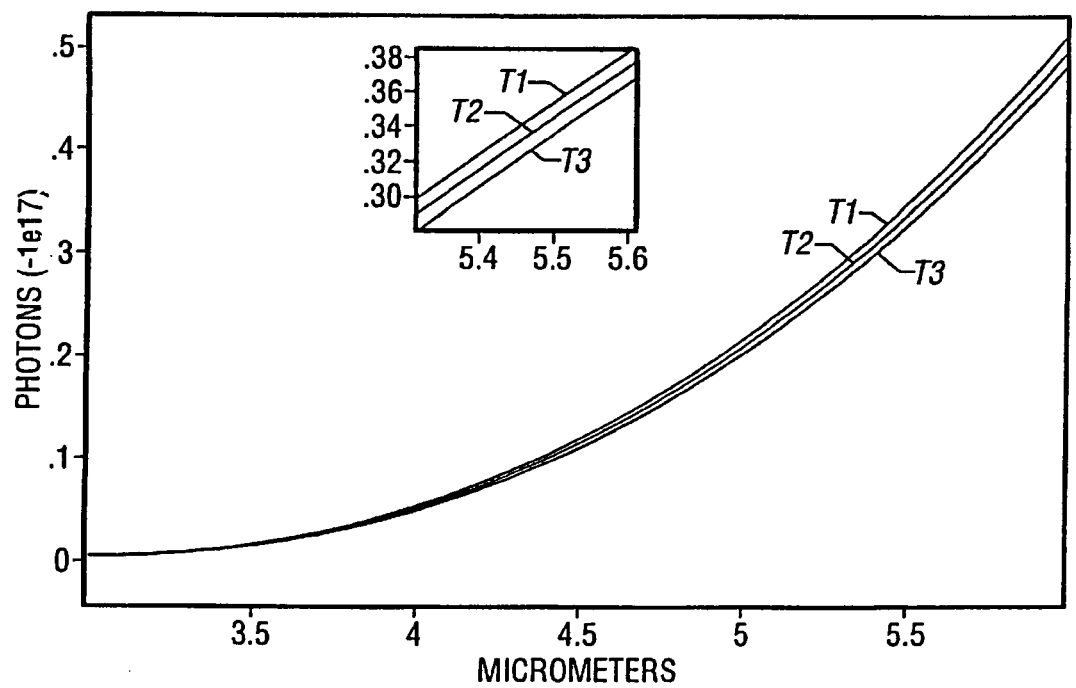
FIG. 2 is a black body curve spectrum for temperatures T1, T2, and T3 (differing sequentially by a single degree Kelvin) plotted as emitted radiation in photons ($\times$1E17) versus wavelength (micrometers).

Referring now to the figures, FIG. 1 shows a preferred embodiment of the apparatus of the invention in use. A catheter apparatus 10 is shown, which can be placed inside an artery (not shown) having with an interior arterial wall (not shown) which possesses a plurality of plaque loci (not shown). The risk of rupture of either of the plaque loci is unknown until the methods and apparatus of the invention are applied.

Guidewire 20 has been surgically inserted into the artery and can be seen to extend both proximally 22 and distally 24. Guidewire 20 can also be seen to proceed through catheter apparatus 10. Guidewire 20 is used to guide the placement of catheter apparatus 10 to the area of the artery which contains plaque loci.

Catheter apparatus 10 comprises at its distal end (the end farthest from the detector) an inflatable balloon 40, a signal fiber 50, and a reference fiber 60. Inflatable balloon 40 is shown in its inflated state, which would cause it to rest firmly against an interior wall of an artery and against plaque loci. Depending upon the natural direction of blood flow within the artery, inflation of balloon 40 would substantially limit flow of blood either at position 32 or 34 or any of the similar points around the perimeter of the generally circular series of contact points between the balloon wall 42 and an interior artery wall, allowing measurements being conducted by catheter apparatus 10 to proceed without interference.

Balloon 40 comprises a wall 42 which is made of an elastic material. The perimeters of balloon 40 are such that inflation causes sealing or closure of the balloon 40 at points along the arterial wall. When deflated, balloon 40 retreats from its contact of the arterial wall, allowing reestablishment of natural blood flow within the artery, and allowing facile movement of catheter apparatus 10 in the artery to a next position, for instance to a position at which catheter apparatus 10 may be used to measure radiation emitted from another plaque locus. Activation of inflation/deflation of balloon 40 may be accomplished in any of a number of ways known well to those of skill in the art of building angioplasty or embolectomy catheters or balloon-tipped catheters.

The purpose of balloon 40 is to avoid problems associated with absorption of infra-red radiation by water between the source of infra-red radiation being measured and the distal catheter portion. Upon inflation and contact of the artery wall, the balloon wall 42 assumes the temperature of the portions of the artery with which it is most proximate. The void area 46 excludes all water between the balloon wall interior and the distal signal fiber tip 56.

Signal fiber 50 has a translucent tip region 52 and an opaque body region 54 which is capable or incapable, respectively, of transmitting infra-red radiation efficiently. Opaque body region 54 may be a region in which signal fiber 50 is covered over by a cladding or sleeve 56 which causes the region to become opaque and incapable of efficiently transmitting or absorbing infra-red radiation. Translucent region 52 may simply be an area in which signal fiber 50 is exposed. Signal fiber 50 is an optical fiber which can efficiently transmit infra-red radiation. In order to collect such radiation from the surrounding milieu, signal fiber 50 may be fitted or otherwise used at its distal end with a collecting device 58 which focuses the infra-red radiation of the surrounding milieu into the fiber for subsequent transmission.

Unlike signal fiber 50, reference fiber 60 has no translucent region. Rather, reference fiber 60 has an opaque end 62 and an opaque region 64, both of which are incapable of transmitting infra-red radiation efficiently. As with the signal fiber 50, reference fiber 60, opaque region 64 may be a region in which reference fiber 60 is covered over by a cladding or sleeve 66 which causes the region to become opaque and incapable of efficiently transmitting or absorbing infra-red radiation. Opaque end 62 may be an area in which reference fiber 60 is coated with an infra-red reflective coating such as polished silver or aluminum. In all other regards, reference fiber 60 is identical to signal fiber 50 in its ability to function as an optical fiber which can efficiently transmit infra-red radiation. It may be used, therefore, to set a baseline in order to compensate for any temperature profile along signal fiber 50 from its distal to its proximal end. As shown in FIG. 1, reference fiber 60 is offset from signal fiber 50 in the proximal direction. This offset (which can be equally well accomplished by offsetting distally) physically introduces a time delay between the radiation received and transmitted by each fiber. As will be discussed immediately below, this time delay is introduced in order to ensure that the signal and reference beams issuing from the proximal ends of each fiber strike the filter on the same spatial portion. By doing so, it is possible to eliminate alignment problems or bandpass dissimilarites arising from a multi-filter system.

When in operation, the fiber-balloon array 70 collects thermal radiation which is transmitted proximally through signal fiber 50 and reference fiber 60. Both fibers are positioned to transmit through spinning radiometer 80 at identical radial position 82 to impinge on digitizers 92 or 90, respectively. Once a digitized signal is generated from each of the optical fiber transmissions, the background signal created by the reference fiber 60 is subtracted by computer 94 from the digitized signal transmitted by the signal fiber 50. The resulting adjusted signal is mathematically fitted by computer 94 to a spectrum of black body curves 96 in order to ascertain the temperature of the particular locus.

Catheter Construction

Several options for materials for the other various components of the catheter devices described herein exist. The key parameters for the optical components are optical transparency, flexibility and strength. Materials such as high strength polyester and polyethylene terephthalate (PET) are very clear and easily extruded in ultrathin wall sizes. A high strength braided polyester is useful for translating twisting motions over long distances as may be required in certain embodiments. Spacers/bearings can be made from Teflon®. The overall flexibility of the catheter will be approximately the same as similar-sized cardiovascular laser, fiberoptic, angioplasty and atherectomizing catheters. These devices should therefore be deliverable to small diameter coronary arteries. A detector will be positioned at the proximal end of the catheter (outside the patient) utilizing InSb or, alternatively, HgCdTe, $TeO_2$, or TAS detection systems.

The elongated flexible fiberoptic element will be connected at one end to an optical connector through a protective sheath. The optical connector is a standard item adapted to be slidably inserted into a thermal detector, and will include a plurality of openings in one side through which fluids or gases, including air, can be introduced into the catheter and emitted therefrom. The connector will also include a coupling element for connecting to a pressure transducer to measure pressure, there being an opening in the connector communicating with the coupling element and the pressure lumen of the catheter. The coupling element may also be connected to a syringe to take a blood sample or to use a saline solution to flush the catheter.

The materials of which catheters are constructed may be any of those commonly used, including flexible plastics such as nylon, Teflon™, vinyls such as polyvinyl chloride, polyurethane, and polyethylene, or various rubber compounds. Typically, the catheter will typically be 5 to 40 inches long and have an outer diameter of about 1 to 2 millimeters. The lumen inside the catheter can vary but typically will be about one half to 1 millimeter in diameter.

The minimum detectable heat differential using the devices and materials of the present invention will be about 0.1° C. While the devices of the invention will be capable of finer thermal discrimination, biological variables are apt to introduce noise into the system. In most instances, plaques which are in danger of rupturing will vary from those less at risk by at least 1.5° C.

At-Risk Plaque

Figure 3:
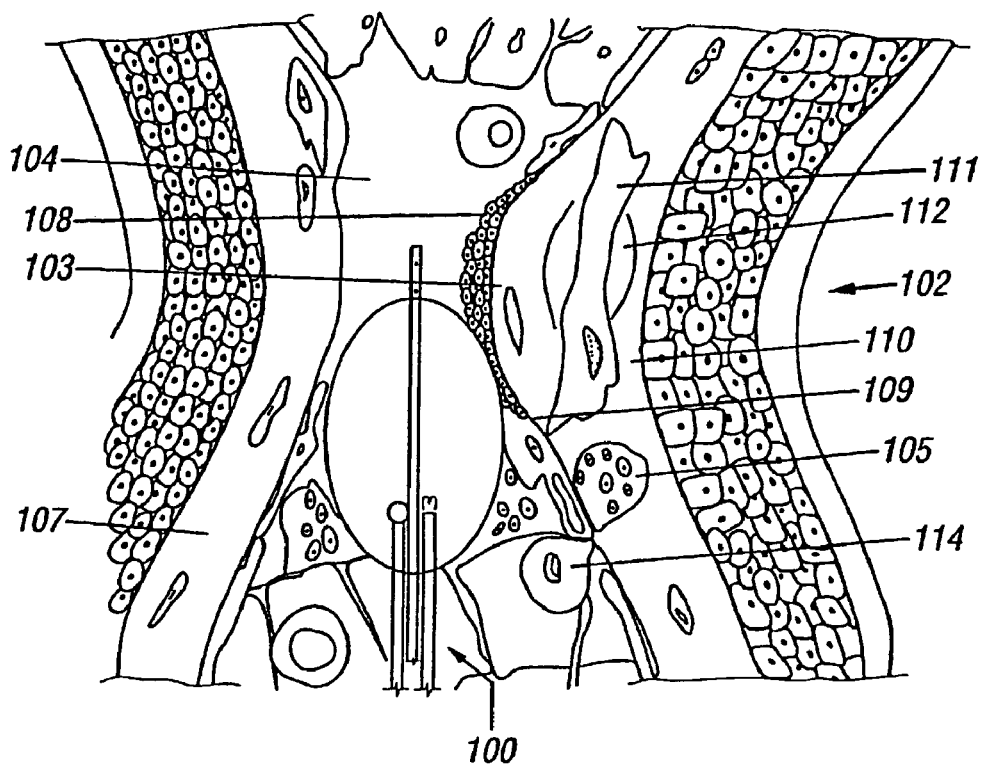
FIG. 3 is a length-wise cross sectional view of the catheter tip of FIG. 1 in place within a blood vessel new a plaque at risk of rupture.

Generally then, as an overview of the device and method of the invention in FIG. 3, the infrared-sensing catheter 100 has identified an ulcerated atherosclerotic plaque 102 which is accompanied by platelet aggregation 103 and vasoconstriction 104. Because of the presence of inflammatory cells 105 in this plaque 102, its temperature is higher than that of the immediately adjacent vessel 107, and this change is sensed by the catheter 100. Some endothelial cells 108 have been lost (as a result of senescence, inflammation, infarction, toxins, or balloon injury) causing platelets 109 to become activated and to adhere to the damaged vessel wall 110. The activated platelets 109 release mediators that cause vasoconstriction, platelet aggregation, and growth of smooth muscle cells; these mediator include ADP, serotonin, thromboxane $A_2$, platelet-derived growth factor, transforming growth factor-β, and PF4. The exposure of subendothelial collagen 111 and lipid 112 and the activation of platelets promote enzymatic activation of coagulation enzymes, which result in the release of plasma mitogens and the activation of thrombin, m enzyme which cleaves fibrinogen to form fibrin. The culmination of this process may be complete occlusion of the artery and consequent injury to the heart (or brain, in the case of a carotid, vertebral or cerebral artery).

Also shown is a monocyte 114, which has attached itself to adhesion molecules on the surface of activated endothelial cells. The monocyte becomes a macrophage involved in uptake of modified cholesterol and the release, as by-products, of mitogens and proteolytic enzymes that may promote rupture.

EXAMPLE I

Methods

Fifty carotid endarterectomy specimens were studied in the living state after gross inspection by a pathologist. Visible thrombi, noted in about 30% of the specimens, were typically removed by gentle irrigation, suggesting that they were surgical artifacts. The indications for surgery were generally a carotid stenosis and transient ischemic attack or stroke.

Twenty-four specimens from 22 patients were examined at room temperature (20° C.). Another 26 specimens from 26 patients were examined in a humidified incubator at 37° C.

Within 15 minutes after removal of a specimen, a Cole-Parmer model 8402–20 thermistor with a 24-gauge needle tip (accuracy, 0.1° C.: time constant, 0.15) was used to measure the temperature of the luminal surface in 20 locations. Temperatures were reproducible (±0.1° C.), and most measurements were found to be within 0.2° C. of each other and thus were designated as the background temperature.

In most plaques, several locations with higher temperature were all found. These locations and the background temperatures were marked with indelible ink of varying colors (recorded, but not coded so as to indicate the temperature to the pathologist) and re-measured to assure reproducibility. Tissues were then fixed in 10% formalin and cut lengthwise, embedded to reveal the intima and media, processed for histology, and stained with hematoxylin and eosin or Masson's trichrome, or immunostained for macrophages using the HAM-56 and KP-1 antibodies (Dako) as previously described. Nikkari, et al., *Circulation* 92:1393–1398 (1995). The cap thickness and the cell density in a 300×400 μm region beneath the dyed regions was measured using a Mackintosh Centris 650 and NIH Image software (version 1.43), available on the Internet from the National Institutes of Health, Bethesda, Md.

Preliminary experiments were also performed with a Jet Propulsion Laboratory platinum silicide camera, which we further calibrated against a Mach 5 scanning infrared camera (Flexi-therm, Westbury, N.Y.),—which in turn was calibrated against beakers of water at various temperatures from 0 to 100° C. with a near perfect correlation, y=0.99x+0.31, where x was the temperature measured by mercury thermometer. The camera had a thermal resolution of 0.10° C. and a spatial resolution of 0.15 mm.

Results

Figure 4A:
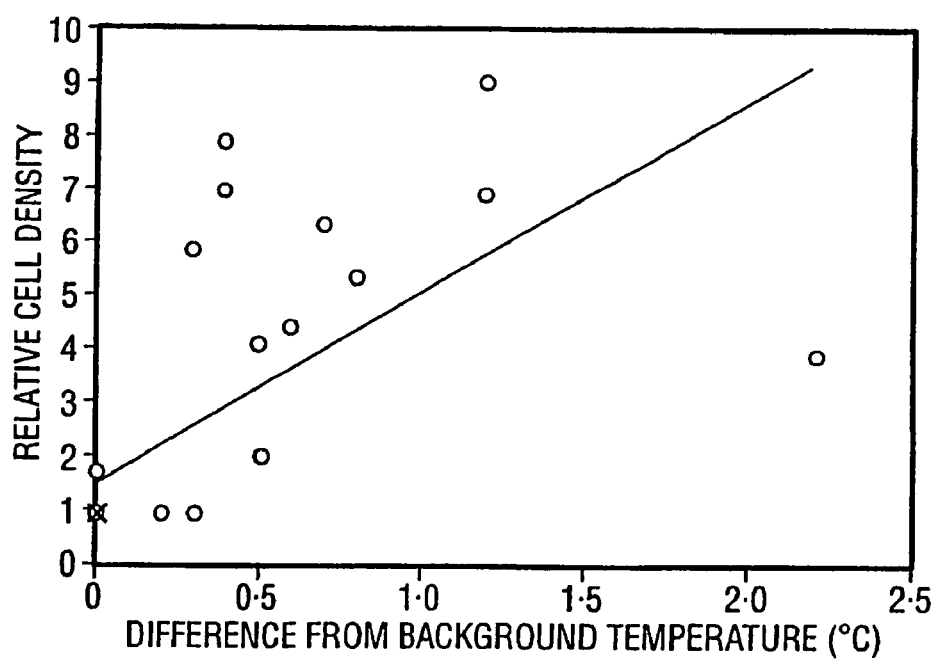
FIG. 4(a) is a graph depicting surface temperature of living carotid artery plaque in relation to cell density. Relative cell density equals the ratio of cell density in the area of interest to that of the background area. Temperature measurements were made at room temperature (20° C.) on 24 samples from 22 patients 10–15 minutes after removal. Point>(O° C. difference in temperature) represents 27 observations.

Plaques exhibited multiple regions in which surface temperatures varied reproducibly by 0.2 to 0.3° C. (±1.0° C.), and 37% of the plaques had 1 to 5 substantially warmer (0.4 to 2.2° C.) regions per plaque. For instance, in typical instances, regions 1 mm apart had a reproducible temperature difference of 0.6° C. Although the lumenal surfaces of the plaques exhibited visible heterogeneity, differences in temperature were not apparent to the naked eye. These temperature differences correlated positively with the underlying density of cells (r=0.68, p=0.0001) (FIG. 4A), most of which were mononuclear cells with the morphologic characteristics and immunoreactivity (with HAM-56 and KP-1) of macrophages.

Several mitotic figures were noted. Some foam cells were noted, but regions predominantly populated by foam cells were cooler (and had lower cell density) than regions with mononuclear infiltrates. Many plaques contained a few lymphocytes and mast cells.

Figure 5:
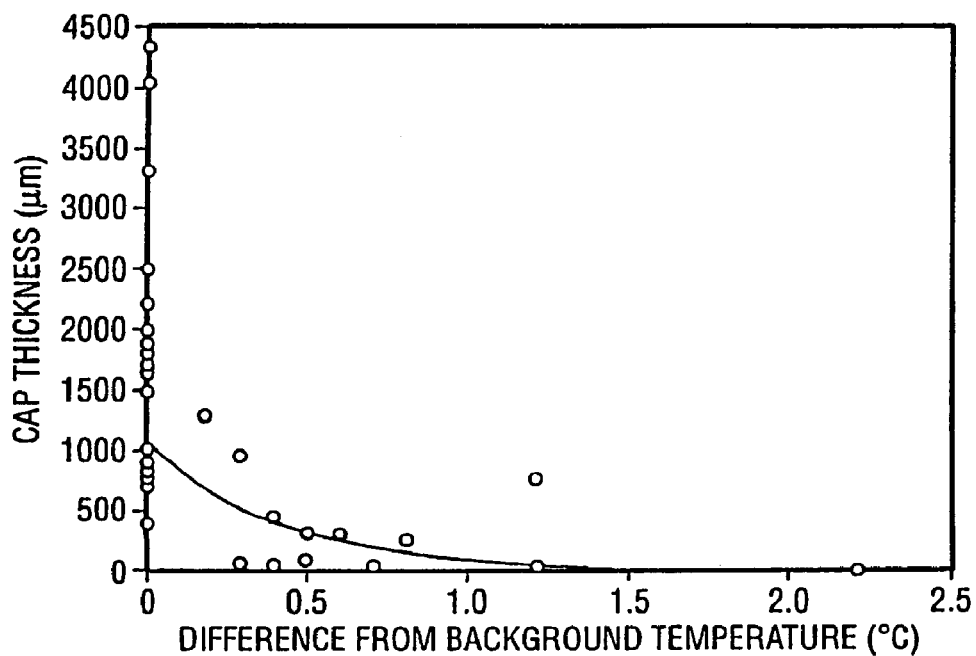
FIG. 5 is a graph depicting plaque surface temperature as a function of cap thickness. Samples that had a non-inflamed fibrous cap were subjected to planimetry to measure distance from the lumen to the center of the underlying cell cluster.

Temperature varied inversely with cap thickness (r=−0.38, p=0.0006) (FIG. 5). The best correlation (r=0.74, p=0.0009) was given by the theoretically expected equation $\Delta T$=relative cell density÷cap thickness. Cooler regions were non-cellular: fresh thromboses, hemorrhage, scar, calcium, or regions of cholesterol pooling without inflammatory infiltration.

The warmer regions were not visibly different on gross inspection, even though many of them had a superficial layer of inflammatory cells, some of which had small aggregations of platelets. Other large areas were free of inflammatory cells but lacked endothelial cells. These had probably been denuded during surgery, since postmortem studies usually show only focal denudation unless there is thrombosis or inflammation. Van Damme, et al., *Cardiovasc Pathol* 3:9–17 (1994).

A minority of plaques (approximately 20%) exhibited no detectable thermal heterogeneity. Regions of deep or superficial inflammation in these specimens were not marked with dye, indicating that the overlying temperature had not been measured. In a few of the regions containing cellular infiltrates, temperatures had been measured, and they were no warmer than less cellular adjacent areas. This finding was believed by the inventors to possibly reflect decreased metabolic activity in specimens that were kept at room temperature for a longer interval after removal.

Figure 4B:
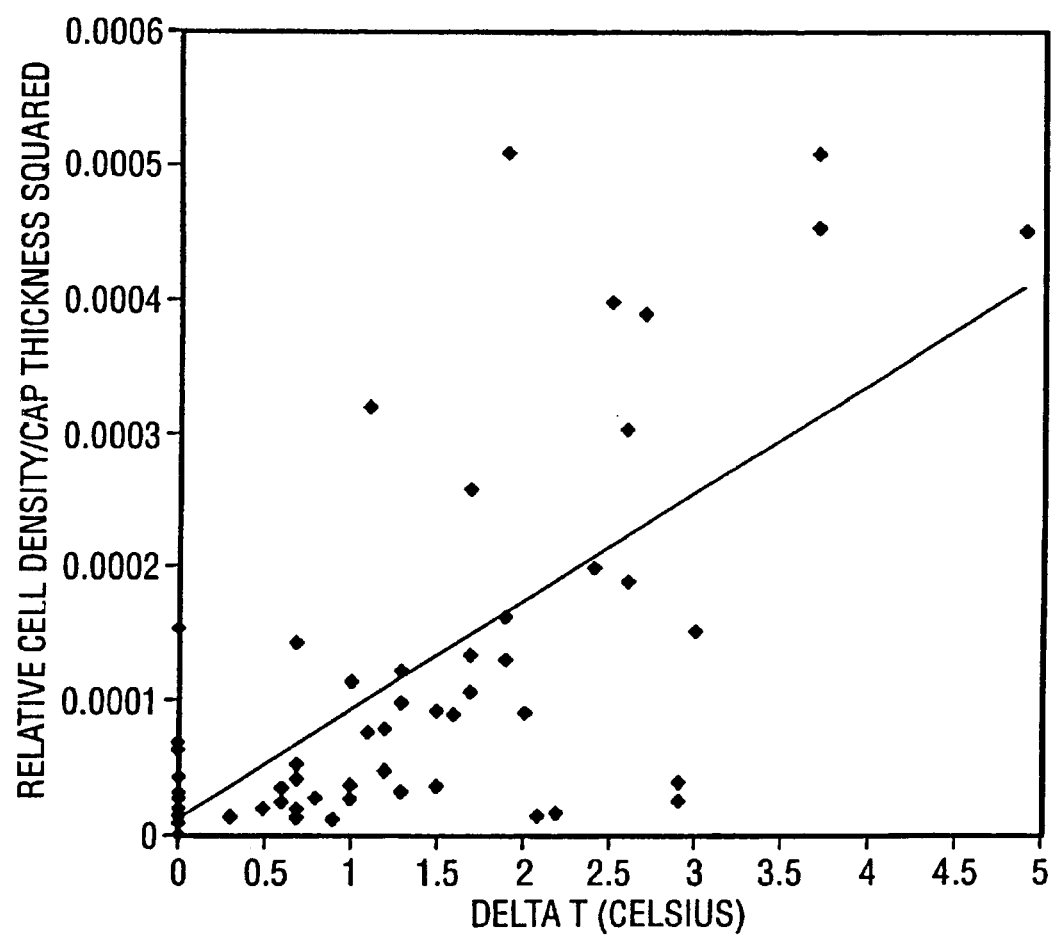
FIG. 4(b) shows the correlation between living human carotid plaque temperature and cell density when measured in a 37° C. chamber.

Therefore, a second series of plaques was analyzed in a 37° C. incubator. These 26 specimens from 26 patients with a mean age of 68 (range, 50 to 86) revealed a considerably closer correlation with cell density (r=0.68, p<0.0001), more thermal heterogeneity (93% of specimens), and a wider range of temperatures, typically 1 to 3° C.; some specimens only 10 mm apart were characterized by temperature differences as great as 4 to 5° C. See, FIG. 4B (points represented by solid diamonds are the relative cell densities divided by the cap thickness squared; linear regression of these points resulted in the solid line shown).

Figure 6:
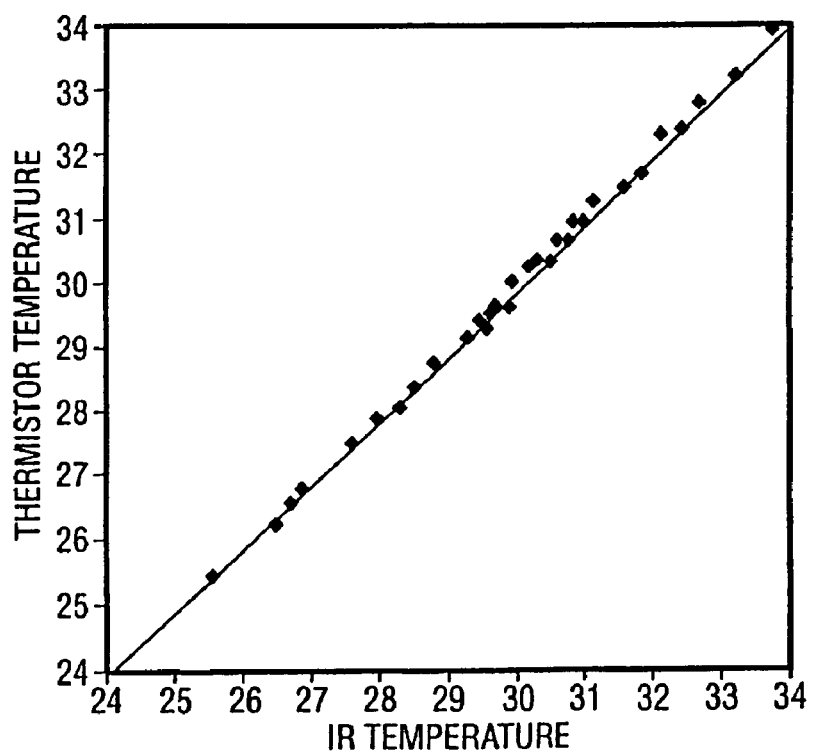
FIG. 6 shows the correlation between thermistor and IR camera measurements in living human carotid plaque specimens (freshly excised, in a 37° C. chamber) where r=0.9885 and p=0.0001.
Figure 7:
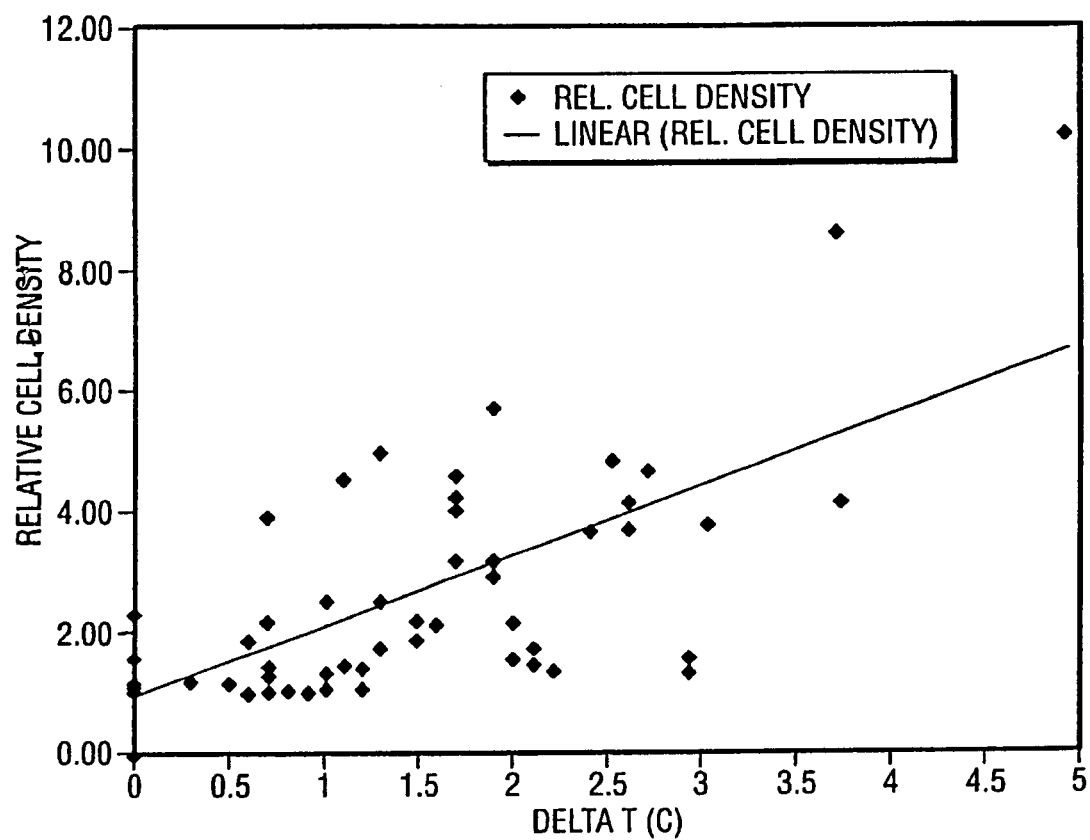
FIG. 7 shows the correlation of IR radiation with cell density in the specimens described in FIG. 6, above.

The inventors also studied several specimens using a platinum silicide, cooled, infrared camera with a thermal resolution of 0.1° C. and a spatial resolution of 0.1 mm. This camera detected thermal heterogeneity in ex vivo specimens. As shown in FIG. 6, the IR camera when used to identify thermally distinct plaque correlated well with direct contact thermistor measurements in freshly excised human carotid artery plaques specimens (r=0.9885, p<0.0001). FIG. 7 shows that this correlation of the IR camera measured temperatures was also observed with cell density measurements. It is noted by the inventors that cooled staring array cameras have even better thermal resolution, and spatial resolutions are as low as 10 $\mu$m.

Conclusions

Most human carotid atherectomy specimens contain foci of increased heat apparently produced by underlying cells, most of which are macrophages. When studied at 37° C., the temperature variation was greater than 20° C., consistent with reduced metabolic activity at 20° C. that makes the plaque more homogeneous in temperature.

In the samples studied at body temperature, a thermistor with a 1-mm tip was able to detect differences as great as 4° C. within different parts of the same plaque that were only 10 mm apart. Temperatures were highest when the cells were closest to the probe (i.e., at or just beneath the lumen itself). Most of the lumenal surfaces of the plaques had several regions characterized by superficial inflammation and endothelial denudation.

Only some areas of surface inflammation were associated with visible thrombosis; most were associated with microscopic thrombosis (e.g., a few fibrin strands and attached platelets) or none at all. These results suggest that increased plaque heat is an indicator of plaques that are denuded and inflamed and consequently at risk of thrombosis.

The inventors also found a few hot regions associated with foci of inflammation just beneath thin but intact caps. Since these plaques are believed to be at increased risk of rupture, it is believed by the inventors that measuring plaque temperature in vivo could enable one to identify such plaques.

EXAMPLE II

Limitations of the Study

A potential confounder identified by the inventors is plaque angiogenesis (neovascularization). The inventors studied living plaques ex vivo. In vivo, the presence and tone of the vasae vasorum might influence the temperature. However, since plaque angiogenesis correlates with inflammation, Nikkari et al., *Circulation* 92:1393–1398 (1995) and both are considered risk factors for plaque rupture, it is likely that temperature will still be predictive in vivo.

The inventors also believe that one must consider that what is true for atherosclerotic plaque in the carotid arteries may not be true in other sites, for example, the coronary arteries. The pathology of the plaque is somewhat different in the two locations. (Van Damme, et al., *Cardiovasc Pathol* 3:9–17 (1994)) and the risk factors are also different. Kannel, *J Cardiovasc Risk* 1:333–339 (1994); Sharrett, et al., *Arterioscler Thromb* 14:1098–1104 (1994).

EXAMPLE III

Potential of Spectroscopy, Tomography, and Interferometry

Infrared spectroscopy could prove useful in several ways. First, it should be able to corroborate the location of macrophages by the massive amounts of nitric oxide they produce, since nitric oxide has a characteristic near-infrared spectrum. Ohdan, et al., *Transplantation* 57:1674–1677 (1994). Near-infrared imaging of cholesterol has already been demonstrated. Cassis, et al., *Anal Chem* 65:1247–1256 (1993). Second, since infrared and near-infrared wavelengths penetrate tissue more deeply as wavelength increases, longer wavelengths should reveal metabolic activity in deeper (0.1- to 1-mm) regions.

This phenomenon could be used to develop computed infrared tomography, possibly in conjunction with interferometry, in which an incident beam is split by a moving mirror to produce a reference beam and a beam that is variably scattered and absorbed by the tissue. The nonsynchronous reflected wavelengths are reconstituted to reveal structural detail with 20-$\mu$m resolution. Benaron, et al., *Science* 259:1463–1466 (1993); Brezinski, et al., *Circulation* 92:1–149 (1995).

EXAMPLE IV

Noninvasive Detection of Plaques at Risk

Alternatives to infrared detection are also desirable since infrared absorption, convection, and tissue emissivity differences are likely to preclude non-invasive infrared tomography. Such alternatives include imaging the inflammatory cells with gallium, (Pasterkamp, et al., *Circulation* 91:1444–1449 (1995)) $^{18}$FDG positron scanning, radiolabeled anti-macrophage antibody fragments, or magnetic resonance (to take advantage of the temperature-dependence of proton-spin relaxation). MacFall, et al., *Int J Hyperthermia* 11:73–86 (1995).

These techniques lack sufficient spatial resolution for detecting inflammatory foci beneath the surface of moving coronary arteries (particularly circumflex and distal vessels) and cannot be used 'on line' to direct plaque-specific interventional therapies. However, the resolution in these techniques may be adequate in thick-walled, relatively stationary arteries such as the aorta, carotid and femoral arteries. Toussaint, et al., *Arterioscler Thromb Vas Biol* 15:1533–1542 (1995); Skinner, et al., *Nature Medicine* 1:69 (1995). If lumenal inflammation can be distinguished from adventitial inflammation, the latter may prove useful in predicting progression of aortic aneurysms.

EXAMPLE V

Therapeutic Implications

Lowering serum cholesterol concentrations by means of diet or drugs can reduce mortality, perhaps because reverse cholesterol transport reduces the size of the lipid core. However, the most convincing trial to date indicates only a 35% decrease in coronary mortality with cholesterol-lowering therapy (and little benefit in women). Scandinavian Simvastatin Survival Study Group, *Lancet* 344: 1383–1389 (1994). This finding suggests that other factors, such as hemostatic variables, are affecting mortality. However, even with the same patient, plaques progress or regress relatively independently. Gould, *Circulation* 90:1558–1571 (1994). This variability suggests that lesion-specific variables (for example, stenosis length, surface thrombosis, low shear stress due to low or turbulent flow, and vasoconstriction) increase the risk of thrombosis. Alderman, et al., *J Am Coll Cardiol* 22:1141–1154 (1993); Nobuyoshi, et al., *J Am Coll Cardiol* 18:904–910 (1991).

If hot plaques producing stenoses in the "non-critical" range of 10% to 70% are shown to be at high risk of rupture, should they undergo angioplasty? If the risk of dilation is similar to that of more severe stenoses (approximately 1% mortality, 2% aorto-coronary bypass), What is the benefit of converting an unstable lesion into one with a 70% chance of long-term patency and a 30% chance of restenosis? Even before the recent trials indicating that stents reduce restenosis rates to 10% to 20%, the large Emory follow-up indicated an identical 96% five-year survival rate in patients with and without restenosis, despite the increased need for repeat angioplasty or bypass surgery in the former group. These data suggest that angioplasty could be beneficial if the near-term risk of sudden (spontaneous) occlusion is only about 5%.

EXAMPLE VI

Medical Therapies

Medical therapies would depend, in part, on whether the inflammation is on the surface or beneath an intact cap. This distinction may one day be made by angioscopy (especially with the use of light-emitting antibodies) or by sampling blood for soluble markers of inflammation (P-selectin, VCAM-1, and others). Magnetic resonance imaging, ultrasound, and near-infrared imaging may also prove helpful.

Therapies might include local delivery of agents (peptides, peptide mimetics, oligonucleotides, and others) that prevent monocyte recruitment, attachment, activation, or DNA synthesis. Conversely, Collagen synthesis might be stimulated with ascorbic acid or transforming growth factor β (which also acts to inhibit angiogenesis, inflammation, and smooth muscle proliferation in most models, though it can also provoke inflammation in non-inflamed tissue and delay endothelial regeneration). Nathan, et al., *J Cell Biol* 113: 981–986 (1991). Endothelial regeneration can be enhanced by basic or acidic fibroblast growth factor or by vascular endothelial growth factor, among others. Casscells, *Circulation* 91:2699–2702 (1995).

In summary, living human carotid atherosclerotic plaques exhibit thermal micro-heterogeneity attributable mainly to macrophages at or near the lumen. These regions of increased temperature can be identified by thermistors and infrared thermography. If hot plaques are indeed at high risk of thrombosis (or restenosis (Gertz. et al., *Circulation* 92:1–293 (1995); Moreno, et al., *Circulation* 92:1–161 (1995)) or—in the case of adventitial inflammation—of aneurynsmal rupture, it may be possible to develop catheter-based and noninvasive means of imaging and treating these potentially life-threatening lesions. These technologies might also be used to detect subepithelial clusters of inflammatory or malignant cells in other organs by magnetic resonance imaging or by endoscopy, ophthalmoscopy, laparoscopy, artheroscopy, or transcranial imaging.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, while the present invention has been supported by examples in the biomedical arts, the apparatus and methods of the invention may be equally well applied to the analysis of wall weaknesses of any vessel so long as such weaknesses exhibit or can be made to exhibit differential heating. Thus, manmade vessels such as conduit, if heated externally may be subjected to internal analysis using the apparatus and methods of the invention. All such modifications are intended to be included within the scope of the appended claims.

What is claimed is:

1. A method of detecting vulnerable arterial plaque formed on the vessel wall in vivo, comprising:
    obtaining an image of the arterial plaque;
    measuring the temperature of the arterial plaque; and
    determining whether the plaque exhibits an elevated temperature compared to the temperature of at least one adjacent vessel wall site.

2. The method of claim 1 wherein said step of obtaining an image comprises obtaining an intravascular ultrasound image of the arterial plaque.

3. The method of claim 1 wherein said step of obtaining an image comprises obtaining a magnetic resonance image of the arterial plaque.

4. The method of claim 1 wherein said step of determining whether the plaque exhibits an elevated temperature comprises the step of determining whether the plaque exhibits an elevated temperature of up to 5° C. above at least one adjacent vessel wall site.

5. The method of claim 1 wherein said step of determining whether the plaque exhibits an elevated temperature comprises the step of determining whether the plaque exhibits an elevated temperature of between 0.4 to 4° C. above at least one adjacent vessel wall site.

6. The method of claim 1 wherein said step of determining whether the plaque exhibits an elevated temperature comprises the step of determining whether the plaque exhibits an elevated temperature of at least 0.1° C. above at least one adjacent vessel wall site.

7. The method of claim 4 wherein said step of determining whether the plaque exhibits an elevated temperature comprises the step of determining whether the plaque exhibits an elevated temperature of at least 1.5° C. above at least one adjacent vessel wall site.

* * * * *

UNITED STATES PATENT AND TRADEMARK OFFICE
CERTIFICATE OF CORRECTION

| | | |
|---|---|---|
| PATENT NO. | : 6,993,382 B2 | Page 1 of 1 |
| APPLICATION NO. | : 10/222342 | |
| DATED | : January 31, 2006 | |
| INVENTOR(S) | : S. Ward Casscells et al. | |

It is certified that error appears in the above-identified patent and that said Letters Patent is hereby corrected as shown below:

TITLE PAGE, ITEM (75) INVENTORS: please delete the following from the list of inventors: "Gregory H. Bearman, Pasadena, CA (US); Michael L. Eastwood, So. Pasadena, CA (US); Timothy N. Krabach, Valencia, CA (US)"

Signed and Sealed this

Sixth Day of November, 2007

JON W. DUDAS
*Director of the United States Patent and Trademark Office*